United States Patent [19]

Brothersen et al.

[11] Patent Number: 4,954,450
[45] Date of Patent: Sep. 4, 1990

[54] METHOD FOR CONTROLLING THE CONCURRENT GROWTH OF TWO OR MORE LACTIC ACID PRODUCING BACTERIA

[75] Inventors: Carl F. Brothersen, Millville, Utah; Willard R. W. Knoespel, Green Bay, Wis.

[73] Assignee: Miles Laboratories, Inc., Madison, Wis.

[21] Appl. No.: 86,155

[22] Filed: Aug. 17, 1987

[51] Int. Cl.$^5$ .................... C12N 1/20; C12P 39/00; C12P 7/56; A23C 19/00
[52] U.S. Cl. .................... 435/252.4; 435/42; 435/139; 435/170; 435/252.1; 435/252.9; 435/253.4; 435/253.6; 435/885; 435/853; 426/7; 426/34; 426/36; 426/42; 426/43
[58] Field of Search .................. 426/7, 34, 36, 42, 43; 435/42, 139, 170, 252.1, 252.4–252.9, 253.4, 253.6, 853, 885

[56] References Cited

U.S. PATENT DOCUMENTS

| | | | |
|---|---|---|---|
| 3,998,700 | 12/1976 | Reinhold et al. | 435/252.4 |
| 4,282,255 | 8/1981 | Sandine et al. | 426/7 |
| 4,622,304 | 11/1986 | Reddy | 435/252.4 |

*Primary Examiner*—Richard A. Schwartz
*Assistant Examiner*—Richard C. Peet
*Attorney, Agent, or Firm*—Paul J. Juettner

[57] ABSTRACT

Disclosed is a method of growing a mixture of two or more species of lactic acid producing bacteria whose growth rates are differently affected by the pH of the nutrient growth medium. The method involves maintaining the pH of the medium at a low level which actively selects for the growth of one species until that species has reached the desired concentration. The pH is then raised to a level that actively selects for the growth of another species and maintained at this level until that species has reached the desired concentration. The method is especially useful for preparing a starter culture for Italian type cheese containing a mixture of coccus and rod bacteria because the ratio of these bacteria, one to the other, can be closely controlled.

1 Claim, No Drawings

METHOD FOR CONTROLLING THE CONCURRENT GROWTH OF TWO OR MORE LACTIC ACID PRODUCING BACTERIA

BACKGROUND OF THE INVENTION

The present invention relates to bulk starters for cheesemaking and, in particular, to a bulk starter which contains both Lactobacillus (rod) and Streptococcus (cocci) organisms. In the commercial production of cheese, large vats of milk are treated with a milk clotting agent such as rennin and inoculated with lactic acid producing bacteria such as Streptococcus lactis, S. cremoris, S. thermophilus, Lactobacillus bulgaricus and L. helviticus. These bacteria are capable of fermenting lactose or similar carbohydrates to produce lactic acid.

The bacteria is generally propagated from a mother culture in large enough quantities of aqueous medium to produce a bulk starter which can then be used for fermenting the final batch of milk to produce cheese as the final product. In a typical procedure, a bulk starter medium is prepared by dissolving a dry powder comprising a nutrient base and a growth stimulant, together with alkali metal phosphate and/or polyphosphate phage control agents in water to a level of about 8% solids. The solution is sterilized and cooled whereupon it is inoculated with the lactic acid producing bacteria which is then allowed to incubate. After incubation, the 'ripened' starter is added to the cheese milk at a level of from about ½ to 2 weight percent. The cheese milk at this point will have a pH of approximately 6.6, however, as the bacteria grow, the acid they produce will gradually lower the pH.

In the manufacture of Italian cheeses such as mozzarella it is the usual practice to employ a combination of starter bacteria. For example, a Streptococcus thermophilus together with one or more lactobacilli such as Lactobacillus bulgaricus may be used. Streptococci are generally referred to as 'cocci' and the lactobacilli as 'rod' bacteria because of their appearance when examined under a microscope. In the manufacture of Italian cheese, the ratio of cocci to rods in the starter should be from about 4:1 to 1:4 for best results in terms of rheological properties and flavor of the resulting cheese. The most desirable ratio for certain operations is about 1:1 and in others an excess of cocci is preferred.

As mentioned above, the growth of the lactic acid producing bacteria will gradually lower the pH of the starter system due to the formation of lactic acid. Too great a lowering of the pH is detrimental because the bacteria's growth is inhibited and cell loss can occur in the case of excess acidity. Accordingly, excess acidity is neutralized during the bacteria's growth cycle either internally such as by incorporating an insoluble buffering agent into the starter media as disclosed in U.S. Pat. No. 4,282,255 or externally by introducing a base (e.g. ammonium hydroxide). In the case of an Italian type cheese starter containing cocci and rods, pH control takes on additional significance because the rods, i.e. lactobacilli, grow at a faster rate than do the cocci at lower pH values. Since the lactobacilli are more acid tolerant than are the cocci, if the culture is maintained at a relatively low pH the rods will grow more rapidly whereas reproduction of cocci is favored at a higher pH. In addition, the rods are more acid tolerant and will not be killed as readily as the cocci at a relatively low pH. This phenomena is discussed in U.S. Pat. No. 4,622,304 which discloses incubating a mixture of rod and coccus organisms without neutralization of acid until the pH of the growth medium drops to a level of from 3.9 to 5.5 and then quickly raising the pH by at least 1 unit with further incubation of the microorganisms until the ratio of cocci to rods is from about 2:1 to 5:1. This system, sometimes referred to as one step neutralization, differs from conventional external pH control where the media's pH is simply maintained at a pre-selected level and is said to result in an increase of the population of organisms in the finished starter over that which is obtainable using internal pH control. However, this system is not totally satisfactory for obtaining the desired ratio of cocci to rods because in this procedure, the pH of the incubating starter traverses a wide range and is never maintained at a pre-selected pH long enough for the rod/cocci ratio to stabilize.

In conventional external methods of neutralization, the pH of the incubating starter is allowed to drop to a pre-determined pH, e.g. 5.0, and then raised about 0.20 pH units. The incubation is allowed to proceed until the pH again drops to 5.0 and then raised to about 5.2. This procedure is repeated until the available nutrients in the medium are utilized. A graph of pH -vs- time for this method would be saw-toothed in appearance. This procedure maintains the pH of the medium in a single narrow range for the entire growth period of the starter and produces a starter with a single cocci:rod ratio depending on the pH range that is maintained. However, the flexibility of this method for producing a wide range of ratios is limited. If the pH is held below 5.0 in order to increase the rod population, the cocci undergo acid damage resulting in a less active starter and increased inoculation rates in the cheese milk. If the pH is maintained at a level of above 5.5 the coccus population are not acid damaged, however, the starter lacks suitable rod population for producing cheese of optimum quality.

U.S. Pat. No. 3,998,700 describes the optimum ratio of cocci to rods for the manufacture of mozzarella as being from about 3:1 to 5:1 but indicates that some latitude is acceptable as long as the ratio is retained in a range of from 2.5:1 to 5.5:1. This patent discloses a media particularly suited for propagating a cocci/rod starter culture which media comprises acid whey solids and sweet whey solids together with non-fat dry milk.

The growth rates of bacteria are also affected by temperature. The growth rate of Lactobacillus sp (rods) is greater than that of streptococcus sp (cocci) at higher temperatures. Conversely, the cocci will propagate faster than the rods at lower temperatures. Thus, combining high temperature with low pH will favor rod growth whereas raising the pH and lowering the temperature of the culturing media will favor the propagation of cocci. While temperature variations will affect the relative growth rate of rod and cocci bacteria, it is pH control that is of primary significance in controlling these growth rates.

It would be desirable and it is an object of the 5 present invention to provide a method for the incubation of a cheese starter system containing cocci and rod type bacteria in which the ratio of the two types of bacteria can be accurately controlled while increasing the total number of organisms in the finished starter.

SUMMARY OF THE INVENTION

The present invention provides an improved method for growing, in a suitable nutrient medium, two or more species of lactic acid producing bacteria whose growth rates are a function of pH such that each species has a growth rate which is affected differently by pH. The improvement comprises growing the bacteria until the acid they produce lowers the pH of the growth medium to a level where growth of one of the bacterial species is favored and maintaining the pH of the growth medium at this level to actively select for the growth of one species over another until this species has achieved the desired concentration and then raising the pH of the growth medium to a second level which is designed to actively select for the growth of another species and maintaining the pH at the second level until this species has achieved the desired concentration.

DESCRIPTION OF THE INVENTION

The present invention is predicated on the discovery that maintaining the pH of a culture medium which has been inoculated with two different organisms within a narrow range will result in a nearly constant growth of the organism that grows best at the selected pH. In other words, when growing two different organisms with different pH growth optima, the growth of one can be stimulated and the growth of the other can be depressed by maintaining the media at the proper pH. This effect can be reinforced by controlling the temperature of the media, so that when the pH is maintained at a level which is preferred by one of the organisms this species' optimal growth temperature is maintained and likewise when pH is modified to provide optimal growth conditions for the other organism, the temperature is adjusted to the level at which this species grows well.

In the situation previously described where rod and cocci are incubated in the same nutrient growth medium to provide a bacterial starter for the manufacture of Italian type cheeses, the pH of the media can be maintained to facilitate growth of rods for a time sufficient to allow them to reach the desired concentration while the growth of the cocci is inhibited. At this point the pH is adjusted to a level which stimulates the growth of the cocci while depressing rod growth. The growth of the starter culture containing both rods and cocci can be carried out at a temperature in the range of from about 35 to 46° C. However, since rods grow best at higher temperatures (44° to 46° C.) the nutrient medium is normally heated to a temperature in this range during the rod growth phase and then lowered to from 36° to 40° C. during the cocci growth phase since the cocci grow fastest within this range of temperatures. The pH and temperature range selected must be sufficiently stimulating to provide a rapidly growing, healthy population of one organism while suppressing the growth of the second without being harmful thereto.

The final population of each type of organism is directly proportional to the time the media is maintained under conditions most favorable to the growth of each particular species. When the pH and temperature are held in a narrow range which tends to favor the growth of one species for a long period of time, the process of the present invention provides a larger population of this species than can be obtained by conventional methods. This is likewise the case when the media conditions are adjusted to stimulate the growth of the other species. Accordingly the ratio of one of the microorganisms in comparison to the other is directly proportional to the time during incubation spent in the pH and (preferably) temperature range needed by each of the species for its maximum growth.

This system provides two advantages over the traditional or one step neutralization processes. First, it provides better control of the ratio between the two types of organisms. With internal pH control and one step neutralization methods, the pH is constantly changing over a wide range. As the pH changes, the growth rates of each organism will change, and since there is no control of the growth rates, there is limited control of the final proportions of the populations of each species therein. With the system of the present invention, the growth rate of each species is controlled by maintaining the conditions for its optimal growth within a narrow range and the ratio of one species to the other is in proportion to the time the growth medium was maintained under conditions which are preferred by each species. Furthermore, in conventional and one step neutralization techniques the pH of the medium can drop to a level that is damaging to one or both of the bacterial species. Using the method of the present invention allows maintenance of the pH at a level that will not damage the cells resulting in a more viable, active starter.

The invention is hereafter explained in more detail for the preparation of a starter useful in the manufacture of Italian type cheese which starter contains both rods and cocci as the lactic acid producing bacteria.

First of all there is provided a suitable nutrient medium in which to grow the bacteria. A suitable medium contains non-fat dry milk, whey powder, yeast hydrolysate, phosphate; all of which is reconstituted with water to about 7.5% solids. The medium is then inoculated with one or more each of a suitable rod and cocci lactic acid producing bacteria. A typical level of inoculation will involve about 0.0035% (v/v) of each bacterial culture. Suitable rod species include, for example, *Lactobacillus bulgaricus* whereas the cocci are typically a *Streptococcus thermophilus*. After inoculation the bacteria are allowed to incubate until the lactic acid they produce lowers the pH of the medium to a level of 4.7 to 5.0 (preferably about 4.8). At this point sufficient neutralizer is continuously added to maintain the pH at this level. Suitable neutralizers include sodium hydroxide, potassium hydroxide, and ammonium hydroxide. Ammonium hydroxide is preferred. As a practical matter, there will be slight variations in the pH level even during this maintenance stage due to the difficulty of maintaining an exactly uniform pH in this dynamic (acid producing) system. Slight variations of no more than about 0.20 pH units can be tolerated. The temperature of the medium can be maintained in the range of from about 35 to 48° C during the entire incubation period, however, better results in terms of increased growth rate and more viable rod populations are achieved if the temperature is maintained at from about 44 to 46° C during the initial (low pH) growth phase because the rods are more thermophilic than are the cocci. The medium is maintained at the low pH and elevated temperature until the desired population of rods is achieved. This will normally take about 4 to 8 hours.

At this point in the incubation procedure the pH is elevated to the level at which the cocci grow best, i.e. a pH within the range of 5.6 to 6.0 preferably from pH 5.5 to 5.8. This is accomplished by the introduction of an appropriate base, preferably ammonium hydroxide, to the culture medium. When the pH reaches the desired level it is maintained until the population of cocci has reached the desired concentration. The time required for this to occur can be shortened by lowering the temperature to the level at which the cocci grow best, i.e. 36° to 40° C. This will normally take from 3 to 8 hours. Here again, some difficulty may be encountered in maintaining the pH at exactly the desired level and minor variations of no more than about ±0.20 (preferably ±0.1) pH units can be tolerated without defeating the intended purpose of the present invention. After incubating for the necessary length of time while maintaining a uniform pH at the high and low levels, the medium is cooled down to about 8° C. to prevent further cell growth and it can be added to the milk vat to thereby introduce the rods in cocci thereto in the proper concentration and in the proper ratio to each other.

In its preferred embodiment, the process of the present invention comprises the following steps:

1. Providing a suitable nutrient growth medium and inoculating it with a seed culture of at least one each of a suitable rod and cocci lactic acid producing bacteria;

2. Incubating the inoculated medium until the pH reaches a level at which the rods grow best and optionally raising the temperature of the medium to the optimal level for rod growth while maintaining the pH constant until the rod population reaches the desired concentration;

3. Raising the pH of the medium to a second level at which the cocci grow best;

4. Maintaining the pH at this second level and optionally lowering the temperature to the optimum level for cocci growth until the cocci population reaches the desired concentration; and 5. Terminating the incubation by allowing the organisms to use all the available nutrients or by cooling the medium to below 30° C. The starter can be kept active for 3 or 4 days by lowering the temperature to 4°-8° C.

While the process can be controlled manually, the various steps, especially steps 2 and 4 in which the pH must be maintained at a constant level in a dynamic (acid producing) system, would require almost full time attention of the operator. Accordingly, the process is particularly adaptable to computerized control. In general such computerized control operates by continuously monitoring the pH and temperature of the culture media from the time the media is inoculated with culture until the finished starter is cooled and ready for use. The system requires implanting a pH electrode and a temperature sensor in the wall of the starter tank such that they are in contact with the media. The signals from these sensors are amplified and sent to a conveniently located processing unit which is programmed with temperature minimum/maximum values and pH minimum/maximum values for each growth stage. If the temperature of the medium falls below the minimum, the processor activates the tank heating system and warms the medium to the proper temperature. Similarly, if the medium temperature rises above the maximum pre-determined temperature, the processor activates the tank cooling system to cool the medium to the proper temperature.

As the microorganisms grow and acid is produced, the pH falls, and when the pH reaches the pre-determined minimum value the processor activates the neutralized system to thereby maintain pH at this level. The culture is allowed to grow, thereby producing more acid. However, periodic injections of neutralizer maintain the pH nearly constant, i.e. variations of no more than 0.2 pH units will take place, i.e. the low pH level of the first growth stage can range from 4.5 to 5.2 and the high pH level of the second stage can range from 5.4 to 6.2. This process is repeated for a pre-determined number of cycles which the processor keeps track of by counting the number of neutralizer injections. These cycles are related to the growth rate of the organism and are, therefore, directly proportional to the concentration of the microorganisms. When the number of cycles equals the programmed value, the processor switches to the pre-determined temperature and pH values for the second growth stage and the process is repeated.

The temperature and pH minimum and maximum values and all other values are programmed into the instrument by the operator through use of a keyboard and display. These values can be changed at any time to accommodate the different growth rates and pH and temperature growth optima of the organisms that may be used to adjust the coccus to rod ratio and thereby compensate for changes in the cheese manufacturing procedure.

When the second growth stage is complete the cooling system is activated thereby lowering the temperature to 4°-8° C. for storage of the finished starter.

The control panel can also be pre-programmed to provide a warning in the event the system fails and allows the pH and/or temperature to fall out of their acceptable ranges.

EXAMPLE I

A starter medium containing the following dry ingredients was reconstituted to 7.5% solids in water:

| | |
|---|---|
| Non-fat dry milk | 5% |
| Whey powder | 80% |
| Yeast hydrolysate | 8% |
| Diammonium phosphate | 5% |
| Monoammonium phosphate | 2% |

The reconstituted media was pasturized at 90° C. for 60 minutes, then cooled and maintained at 40° C. At this point the medium was inoculated with 0.0125% v/v each of two defined single strains of *S. thermophilus* and two defined single strains of *L. bulgaricus*. The cultures were allowed to gro until the pH dropped to 4.7 whereupon it was maintained at a level between 4.7 and 4.9 for 1 hour. At this point it was raised and maintained at a level between 5.3 and 5.5 for 3½ hours. The medium was then cooled and the cocci to rod ratio was determined by microscopic examination.

EXAMPLE II

A culture medium was prepared and incubated with cultures in the manner described for Example I. The bacteria were allowed to grow until the pH dropped to 5.0 and the pH was then maintained between 5.0 and 5.2 for 3 hours. At this point the pH was raised to 5.5 and maintained between 5.5. and 5.7 for 4 hours. The medium was then cooled and the cocci to rod ratio determined by microscopic examination.

EXAMPLE III

A culture medium was prepared and inoculated as described in the previous examples except that the temperature was maintained between 42° and 43° C. during the first growth stage in which the pH was allowed to drop to 4.6 and maintained between 4.6 and 4.8 for 2½ hours. During the second growth stage the temperature was lowered and maintained between 38°–39° C. while the pH was maintained between 5.6 and 5.8. The second growth stage was maintained for 3 hours after which period the medium was cooled and the cocci to rod ratio determined by microscopic examination.

The growth parameters and cocci to rod ratios for all three experiments are set out in Table I.

TABLE I

|  | I | II | III |
|---|---|---|---|
| Initial pH | 6.2 | 6.2 | 6.2 |
| Time to first ammonia injection (hr.) | 4.2 | 5.3 | 5.7 |
| Growth Stage I |  |  |  |
| pH range | 4.7–4.9 | 5.0–5.2 | 4.6–4.8 |
| Temp. range (°C.) | 40–41 | 40–41 | 42–43 |
| Time (hours) | 1.0 | 3.0 | 2.5 |
| Growth Stage II |  |  |  |
| pH range | 5.3–5.5 | 5.5–5.7 | 5.6–5.8 |
| Temp. range (°C.) | 40–41 | 40–41 | 38–39 |
| Time (hours) | 3.5 | 4.0 | 3.0 |
| Total Time (hours) | 8.7 | 12.3 | 11.2 |
| Cocci to Rod Ratio | 40/60 | 80/20 | 60/40 |

From the data presented in Table I it can be determined that by controlling the growth pH and temperature at which the starter is maintained the coccus to rod ratio in the finished starter can be controlled. It was the purpose of the experiments represented by Table I to coordinate the parameters in growth stages I and II with the resulting ratios of cocci to rods. One can predetermine the parameters necessary to obtain a desired ratio for particular strains of cocci and rods if the operator has some familiarity with these strains. This is accomplished by first making an approximation of the parameters necessary in growth stages I and II to achieve the pre-determined ratio and then incubate the culture using these parameters whereupon the ratio obtained thereby is determined. The results of this trial run are then used to fine tune the parameters necessary to achieve the desired ratio of cocci to rod. If the operator is intimately familiar with the particular strains being used a single run is sufficient for fine tuning. Absent this familiarity, two or three runs may be necessary, but by no means is undue experimentation necessary for determination of the proper ratio.

What is claimed is:

1. A method of growing a mixture of lactic acid producing *Lactobacillus bulgaricus* or *L. helviticus* and *Streptococcus thermophilus* in a suitable nutrient medium which comprises:
    (a) allowing the mixture of bacteria to grow at a temperature of from 44° to 46° C. until the lactic acid produced thereby lowers the pH of the medium to a level of from 4.7 to 5.0;
    (b) maintaining the pH within the range specified in step (a) ±0.2 pH units while maintaining the temperature of the medium at a level of from about 44° to 46° C. for a time sufficient for the Lactobacillus sp. to grow to the desired concentration;
    (c) adding neutralizer to the medium to raise the pH to a level of from 5.4 to 6.0; and
    (d) maintaining the pH within the range specified in step (c) ±0.2 pH units while maintaining the temperature of the medium at a level of from about 36° to 40° C. until the *S. thermophilus* grow to the desired concentration; and
    (e) cooling the medium to a level where further growth of the bacteria is inhibited.

* * * * *